United States Patent
Li et al.

(10) Patent No.: US 10,836,786 B2
(45) Date of Patent: Nov. 17, 2020

(54) CRYSTAL FORM OF DAPAGLIFLOZIN INTERMEDIATE AND PREPARATION METHOD THEREFOR

(71) Applicant: Jiangsu Hansoh Pharmaceutical Group Co., Ltd., Lianyungang (CN)

(72) Inventors: Xiang Li, Jiangsu (CN); Jun Yu, Jiangsu (CN); Haizhou Yu, Jiangsu (CN); Jinjia Wang, Jiangsu (CN); Lei He, Jiangsu (CN); Zuyin Du, Jiangsu (CN)

(73) Assignee: Jiangsu Hansoh Pharmaceutical Group Co., Ltd., Jiangsu (CN)

( * ) Notice: Subject to any disclaimer, the term of this patent is extended or adjusted under 35 U.S.C. 154(b) by 0 days.

(21) Appl. No.: 16/317,636

(22) PCT Filed: Jul. 21, 2017

(86) PCT No.: PCT/CN2017/093833
§ 371 (c)(1),
(2) Date: Jan. 14, 2019

(87) PCT Pub. No.: WO2018/014866
PCT Pub. Date: Jan. 25, 2018

(65) Prior Publication Data
US 2019/0284220 A1    Sep. 19, 2019

(30) Foreign Application Priority Data
Jul. 22, 2016    (CN) .......................... 2016 1 0587582

(51) Int. Cl.
| C07H 7/04 | (2006.01) |
| C07H 15/04 | (2006.01) |
| C07H 1/00 | (2006.01) |
| C07D 309/10 | (2006.01) |
| A61P 3/10 | (2006.01) |

(52) U.S. Cl.
CPC .................. *C07H 7/04* (2013.01); *A61P 3/10* (2018.01); *C07D 309/10* (2013.01); *C07H 1/00* (2013.01); *C07H 15/04* (2013.01); *C07B 2200/13* (2013.01)

(58) Field of Classification Search
None
See application file for complete search history.

(56) References Cited

U.S. PATENT DOCUMENTS

2005/0209166 A1* 9/2005 Eckhardt .............. A61K 9/2018
514/23

FOREIGN PATENT DOCUMENTS

| CN | 104109179 A | 10/2014 |
| CN | 105481915 A | 4/2016 |
| WO | 2008/002824 A1 | 1/2008 |
| WO | 2013/152654 A1 | 10/2013 |
| WO | 2015/132803 A2 | 9/2015 |

OTHER PUBLICATIONS

Int'l Search Report dated Sep. 28, 2017 in Int'l Application No. PCT/CN2017/093833.

* cited by examiner

*Primary Examiner* — Layla D Berry
(74) *Attorney, Agent, or Firm* — Ice Miller LLP

(57) ABSTRACT

Disclosed are a crystal form of a dapagliflozin intermediate and a preparation method therefor, and specifically disclosed are a crystal form of the dapagliflozin intermediate (2S,3R,4S,5S,6R)-2-(4-chloro-3-(4-ethoxybenzyOphenyl)-2-ethoxy-6-(methylhydroxyl) tetrahydro-2H-pyran-3,4,5-triol and a preparation method therefor. The advantages thereof lie in that an intermediate can be highly purified to obtain a sample with a purity of 99.3% or more, which has an important significance for improving the quality of the dapagliflozin, and the preparation process is simple and suitable for industrial production.

18 Claims, 2 Drawing Sheets

CRYSTAL FORM OF DAPAGLIFLOZIN INTERMEDIATE AND PREPARATION METHOD THEREFOR

CROSS-REFERENCE TO RELATED APPLICATION

This application is a Section 371 of International Application No.
PCT/CN2017/093833, filed Jul. 21, 2017, which was published in the Chinese language on Jan. 25, 2018, under International Publication No. WO 2018/014866 A1, which claims priority under 35 U.S.C. § 119(b) to Chinese Patent Application No. 201610587582.7, filed on Jul. 22, 2016, the disclosures of which are incorporated herein by reference in their entireties.

FIELD OF THE INVENTION

The present invention belongs to the field of chemistry, and relates to crystal form A of a key intermediate of dapagliflozin and a method for preparing the same. Specifically, the present invention relates to a crystal form of (2S,3R,4S,5S,6R)-2-(4-chloro-3-(4-ethoxybenzyl)phenyl)-2-ethoxy-6-(methylhydroxy)tetrahydro-2H-pyran-3,4,5-triol and a method for preparing the same.

BACKGROUND OF THE INVENTION

Dapagliflozin, i.e., 2-chloro-5-(β-D-glucopyranosyl-1-yl)-4'-ethoxydiphenylmethane, has the structural formula shown in formula (2):

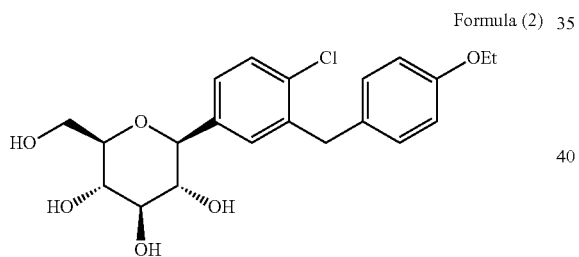

Formula (2)

Dapagliflozin, developed by Bristol-Myers Squibb and AstraZeneca, is used for the treatment of type II diabetes (a sodium-glucose cotransporter-2 (SGLT-2) inhibitor).

Bristol-Myers Squibb and AstraZeneca submitted an application to the European Medicines Agency (EMA) in December 2010, and the European committee for medicinal products for human use recommended the approval of dapagliflozin for the treatment of type II diabetes in April 2012.

Diabetes is a group of endocrine-metabolic diseases having a common marker of high blood sugar. Absolute or relative insufficiency of insulin secretion causes metabolic disorders of sugar, protein, fat and secondary water, and electrolyte. Diabetes can involve chronic damages and dysfunctions of various systems throughout the body, especially eye, kidney, heart, blood vessels and nerves, and can even induce a number of fatal complications. With the aging of the world's population, diabetes has become a common and frequently-occurring disease, which seriously endangers human health. Research data show that the number of diabetic patients worldwide has increased from 150 million in 2000 to 280 million. It is estimated that there will be nearly 500 million diabetic patients worldwide by 2030.

Glucose transporter regulates and controls the balance of glucose metabolism in the normal state of human body. Sodium-glucose cotransporter (SGLT) is a known glucose transporter. SGLT includes SGLT1 and SGLT2. SGLT1 is expressed in small intestine and the distal S3 segment of renal proximal convoluted tubules, and absorbs about 10% of the glucose. SGLT2 is mainly expressed in the proximal SI segment of renal proximal convoluted tubules, and is responsible for more than 90% of glucose reabsorption. Therefore, inhibition of SGLT, particularly SGLT2, can inhibit the reabsorption of sugar, thereby allowing the sugar to be excreted in the urine and lowering the concentration of sugar in the blood.

It is known to those skilled in the art that purification of a drug is generally achieved by crystallization. However, dapagliflozin is difficult to form a crystal, and the purification effect of crystallization is not satisfactory, resulting in difficulty in preparing dapagliflozin with high purity. As a drug for human use, impurities often have adverse effects on the human body, therefore drugs with high purity are an important object for drug development.

Patent application WO2008002824 discloses crystal forms Ig and If of intermediate compound B of dapagliflozin. The dimethanol crystal form Ig loses crystallinity when being left open for a few hours, and the butynediol crystal form If also loses crystallinity when being dried at 30° C. under vacuum, therefore, the stability of both crystal forms is poor. Meanwhile, the purity of dapagliflozin prepared from the compound B disclosed in this patent application is not high, only an oil is obtained after concentration under reduced pressure, and further purification by acetylation is required.

The process is complicated and the yield is not high.

A dapagliflozin intermediate with high purity is essential for obtaining dapagliflozin with high purity. The purity of a dapagliflozin intermediate obtained by a conventional preparation process is about 90%. The reaction using a dapagliflozin intermediate with such a low purity can only produce dapagliflozin with even lower purity. The purification of dapagliflozin intermediate by column chromatography is costly and inefficient, which is not conducive to industrial production. With respect to the purification by crystallization, the dapagliflozin intermediate is difficult to form a crystal due to the structure itself. Therefore, there is an urgent need to develop a dapagliflozin intermediate that can be purified by crystallization and has a stable chemical property, thereby making the purification of dapagliflozin easier and simpler.

SUMMARY OF THE INVENTION

The present invention provides a dapagliflozin intermediate in order to solve the above technical problems.

The chemical name of the dapagliflozin intermediate according to the present invention is (2S,3R,4S,5S,6R)-2-(4-chloro-3-(4-ethoxybenzyl)phenyl)-2-ethoxy-6-(methylhydroxy)t etrahydro-2H-pyran-3,4,5-triol, and the structural formula is shown in formula (1):

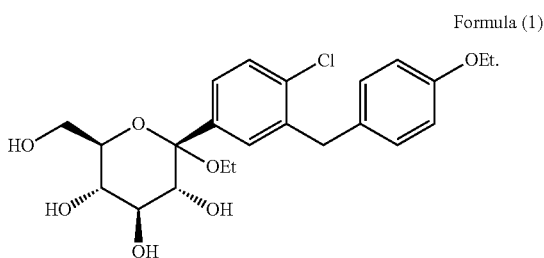 [SMILES: CCOc1ccc(Cc2cc([C@]3(OCC)O[C@H](CO)[C@@H](O)[C@H](O)[C@H]3O)ccc2Cl)cc1]

Formula (1)

Another objective of the present invention is to provide crystal form A of the compound of formula (1).

The objective of the present invention is achieved by the following technical solutions:

The present invention provides the crystal form A of the compound of formula (1), the X-ray powder diffraction (XRPD) spectrum of which comprises characteristic peaks at 2θ values of 5.5±0.2, 13.0±0.2, 15.0±0.2, 17.0±0.2°, 18.3±0.2°, 20.6±0.2°, 21.6±0.2° and 23.1±0.2°.

Preferably, the X-ray powder diffraction spectrum of crystal form A of the compound of formula (1) according to the present invention comprises characteristic peaks at 2θ values of 5.5±0.2°, 9.7±0.2°, 11.7±0.2°, 13.0±0.2°, 14.2±0.2°, 15.0±0.2°, 16.4±0.2°, 17.0±0.2°, 18.3±0.2°, 19.7±0.2°, 20.6±0.2°, 21.6±0.2°, 23.1±0.2°, 23.7±0.2°, 24.5±0.2°, 25.0±0.2°, 25.8±0.2°, 26.3±0.2°, 28.7±0.2°, 29.9±0.2°, 30.6±0.2°, 31.2±0.2° and 32.1±0.2°.

Further preferably, the crystal form A of the compound of formula (1) according to the present invention comprises n-propanol in an amount of about 0-15%, preferably 5%-10%, and more preferably 5%-7.5%, and the unit is in a mass ratio. The XRPD spectrums of crystal form A with different n-propanol contents are consistent with FIG. 1.

Further preferably, a typical example of crystal form A of the compound of formula (1) according to the present invention has the XRPD spectrum as shown in FIG. 1.

Further preferably, a typical example of crystal form A of the compound of formula (1) according to the present invention has the thermogravimetric analysis (TGA) spectrum as shown in FIG. 2.

Another objective of the present invention is to provide a method for preparing the crystal form A of the dapagliflozin intermediate.

The method for preparing the crystal form A of the compound of formula (1) according to the present invention comprises a step of precipitating a crystal from an alcohol solution containing 0.1 g/ml-2.0 g/ml of the compound of formula (1) at 0-30° C.

The method for preparing the crystal form A of the compound of formula (1) according to the present invention comprises the steps of precipitating a crystal from an alcohol solution containing 0.1 g/ml-2.0 g/ml of the compound of formula (1) at 0-30° C., and adding dropwise a $C_{5-8}$ hydrocarbon to the n-propanol solution at the same temperature.

Specifically, the compound of formula (1) was dissolved in an alcohol solution, the concentration of which is about 0.1 g/ml-1.0 g/ml, preferably 0.1 g/ml-0.56 g/ml, and more preferably 0.20 g/ml-0.50 g/ml. The n-propanol solution containing the above compound of formula (1) is left to stand or stirred to precipitate a crystal. In particular, when an excess of n-propanol is added to the compound of formula (1), the mixture can be heated at about 30° C.-60° C. to dissolve the compound, then the mixture is concentrated under reduced pressure to obtain a specific concentration of about 0.1 g/ml-2.0 g/ml.

The method for preparing the crystal form A of the compound of formula (1) according to the present invention can also comprise a step of adding a seed crystal to the solution. The seed crystal can be added before or during the addition of the $C_{5-8}$ hydrocarbon to the solution.

In the method for preparing the crystal form A of the compound of formula (1) according to the present invention, the seed crystal was obtained by dissolving the compound of formula (1) in n-propanol, adding dropwise n-heptane and precipitating a crystal at low temperature.

Preferably, a typical example of preparing the seed crystal of the present invention comprises: about 1 g of the compound of formula (1) was weighed and added to a reactor, 2.0 mL of n-propanol was added at room temperature, the sample was dissolved until the mixture was clear, the mixture was then left to stand at −20° C. to precipitate a solid after two days, 5 ml of n-heptane was added to the above reactor, after being stirred for 24 hours, and the suspension was filtered to obtain a solid that can be used as the seed crystal.

In the method for preparing the crystal form A of the compound of formula (1) according to the present invention, the compound of formula (1) can be an oily or amorphous compound of formula (1).

In the method for preparing the crystal form A of the compound of formula (1) according to the present invention, the crystallization temperature is about 0° C.-30° C., preferably 10° C.-25° C., and more preferably 20° C.-25° C.

In the method for preparing the crystal form A of the compound of formula (1) according to the present invention, the crystallization time is about 0.5 h-12 h, and preferably 6 h-12 h.

In the method for preparing the crystal form A of the compound of formula (1) according to the present invention, water can also be added to the n-propanol solution, the volume of the added water is 0.05-0.5 times, preferably 0.1-0.2 times the mass of the compound of formula (1).

In the method for preparing the crystal form A of the compound of formula (1) according to the present invention, the $C_{5-8}$ hydrocarbon is selected from the group consisting of n-pentane, n-hexane, n-heptane and n-octane, and preferably n-heptane.

In the method for preparing the crystal form A of the compound of formula (1) according to the present invention, the volume of the $C_{5-8}$ hydrocarbon is 2-40 times, preferably 8-25 times, and more preferably 11-20 times the mass of the compound of formula (1).

In the method for preparing the crystal form A of the compound of formula (1) according to the present invention, the crystal form can be separated by filtration, centrifugation and the like. The separated crystal form can be dried by methods such as vacuum drying, direct drying, air drying and the like.

The crystal form A of the compound of formula (1) according to the present invention has a high purity and good stability, and greatly promotes the purification of dapagliflozin. The method for preparing the crystal form A of the compound of formula (1) according to the present invention has a simple and controllable process, and good reproducibility. The method can effectively separate and purify the intermediate from the reaction solution, remove impurities generated during the reaction, and increase the purity of the intermediate from 90% to more than 99.3%.

DETAILED DESCRIPTION OF THE INVENTION

The specific embodiments of the present invention are further described in detail below with reference to the drawings and examples. The following examples are intended to illustrate the present invention, but are not intended to limit the scope of the present invention.

Example 1 Crystal Form A of the Compound of Formula (1)

About 5 g of (2S,3R,4S,5 S,6R)-2-(4-chloro-3-(4-ethoxybenzyl)phenyl)-2-ethoxy-6-(methylhydroxy)t etrahydro-2H-pyran-3,4,5-triol in amorphous form (HPLC purity: 90.24%) were weighed and added to a reactor. 10.0 mL of n-propanol were added at room temperature to dissolve the sample until the solution was clear. The solution became cloudy after the addition of 40 ml of n-heptane, and the seed crystal was added. After stirring for 6 hours at room temperature, the suspension was filtered and dried to obtain the crystal form A of (2S,3R,4S,5 S,6R)-2-(4-chloro-3-(4-ethoxybenzyl)phenyl)-2-ethoxy-6-(methylhydroxy)tetrahydro-2H-pyran-3,4,5-triol (HPLC purity: 99.45%).

Example 2 Crystal form A of the Compound of Formula (1)

Figure 1:
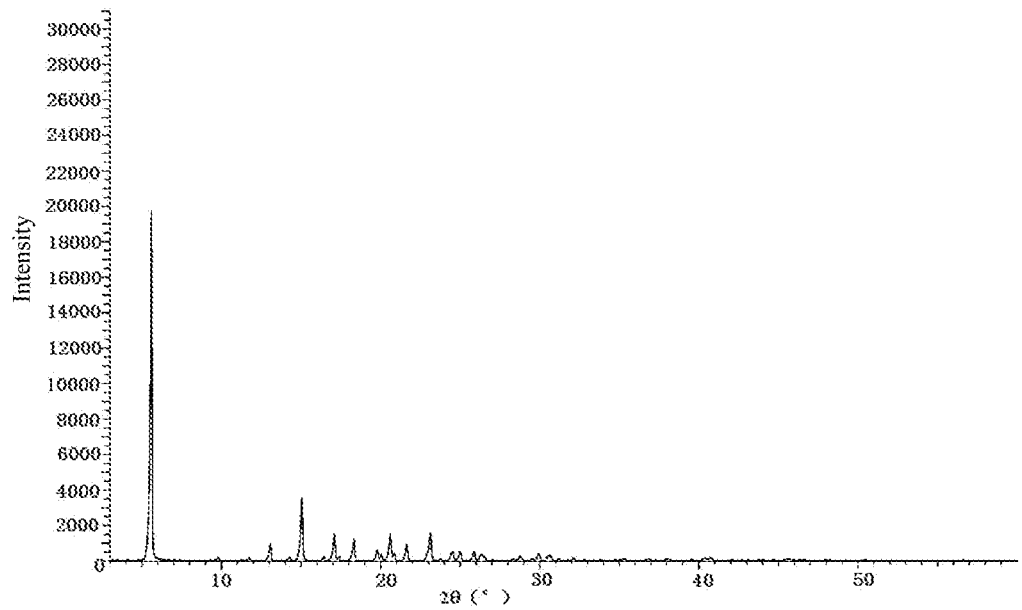
FIG. 1 is the X-ray powder diffraction spectrum of crystal form A of the compound of formula (1) of Example 1.
Figure 2:
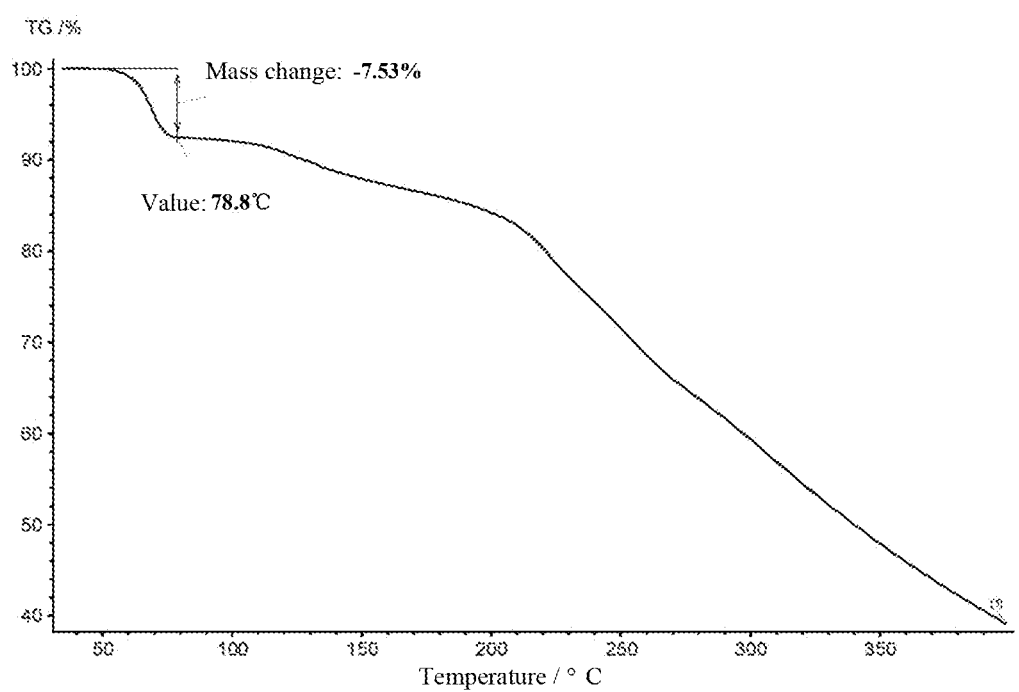
FIG. 2 is the TGA spectrum of crystal form A of the compound of formula (1) of Example 1.
Figure 3:
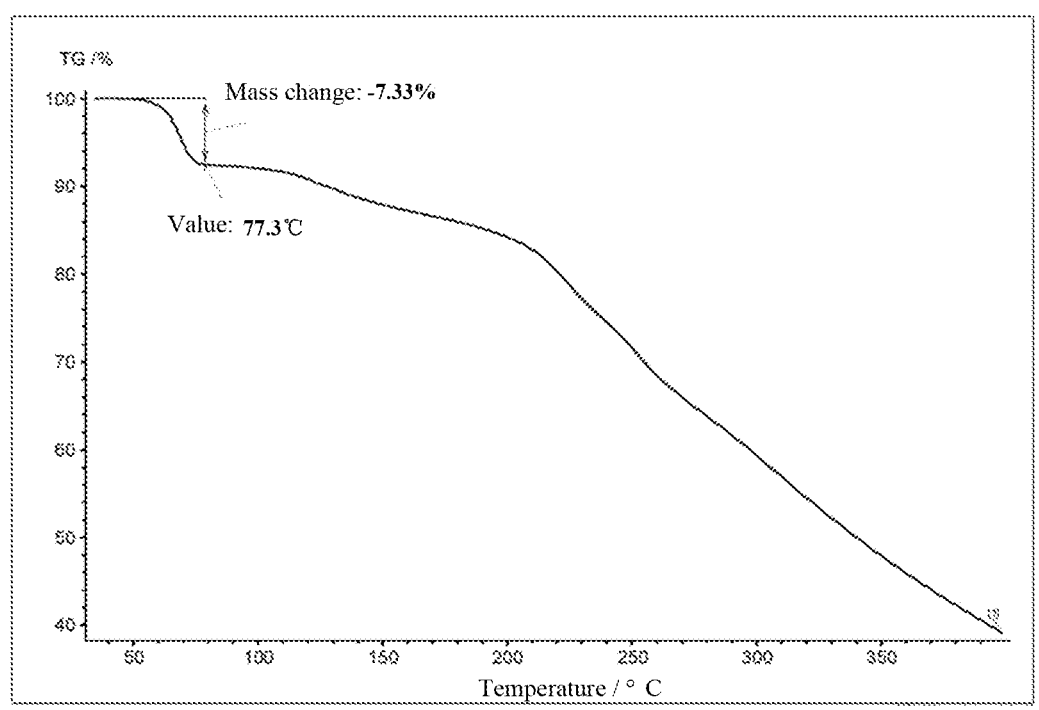
FIG. 3 is the TGA spectrum of crystal form A of the compound of formula (1) of Example 2.

About 4.5 g of (2S,3R,4S,5 S,6R)-2-(4-chloro-3-(4-ethoxybenzyl)phenyl)-2-ethoxy-6-(methylhydroxy)t etrahydro-2H-pyran-3,4,5-triol in amorphous form (HPLC purity: 90.24%) were weighed and added to a reactor. 8.0 mL of n-propanol were added at 60° C. to dissolve the sample until the solution was clear. The solution was stirred and naturally cooled to room temperature, then 30 ml of n-heptane were added at 0° C., and the solution was stirred for about 0.5 hour to precipitate a solid. After adding 20 ml of n-heptane and stirring for 6 hours, the suspension was filtered and dried to obtain the solid crystal form A (HPLC purity: 99.32%). The XRPD spectrum is shown in FIG. 1.

Example 3 Crystal Form A of the Compound of Formula (1)

About 2 g of (2S,3R,4S,5S,6R)-2-(4-chloro-3-(4-ethoxybenzyl)phenyl)-2-ethoxy-6-(methylhydroxy)t etrahydro-2H-pyran-3,4,5-triol in amorphous form (HPLC purity: 90.24%) were weighed and added to a reactor. 10.0 mL of n-propanol were added at 50° C. to dissolve the sample until the solution was clear. The solution was stirred and naturally cooled to room temperature, then 50 ml of n-heptane were added at 0° C. After stirring for 10 hours, the suspension was filtered and dried to obtain the solid crystal form A (HPLC purity: 99.35%). The XRPD spectrum is shown in FIG. 1.

Example 4 Crystal Form A of the Compound of Formula (1)

About 5 g of (2S,3R,4S,5S,6R)-2-(4-chloro-3-(4-ethoxybenzyl)phenyl)-2-ethoxy-6-(methylhydroxy)tetrahydro-2H-pyran-3,4,5-triol in amorphous form (HPLC purity: 90.24%) were weighed and added to a reactor. 10.0 mL of n-propanol were added at room temperature to dissolve the sample until the solution was clear. The solution became cloudy after the addition of 100 ml of n-heptane, and the seed crystal was added. After stirring for 8 hours at room temperature, the suspension was filtered and dried to obtain the solid crystal form A (HPLC purity: 99.30%). The XRPD spectrum is shown in FIG. 1.

Example 5 Crystal Form A of the Compound of Formula (1)

About 10 g of (2S,3R,4S,5 S,6R)-2-(4-chloro-3-(4-ethoxybenzyl)phenyl)-2-ethoxy-6-(methylhydroxy)tetrahydro-2H-pyran-3,4,5-triol in amorphous form (HPLC purity: 90.24%) were weighed and added to a reactor. 40.0 mL of n-propanol and 1 mL of water were added at room temperature to dissolve the sample until the solution was clear. The solution became cloudy after the addition of 20 ml of n-heptane, and the seed crystal was added. After stirring for 6 hours at room temperature, the suspension was filtered and dried to obtain the solid crystal form A (HPLC purity: 99.36%). The XRPD spectrum is shown in FIG. 1.

Example 6 Preparation of Dapagliflozin

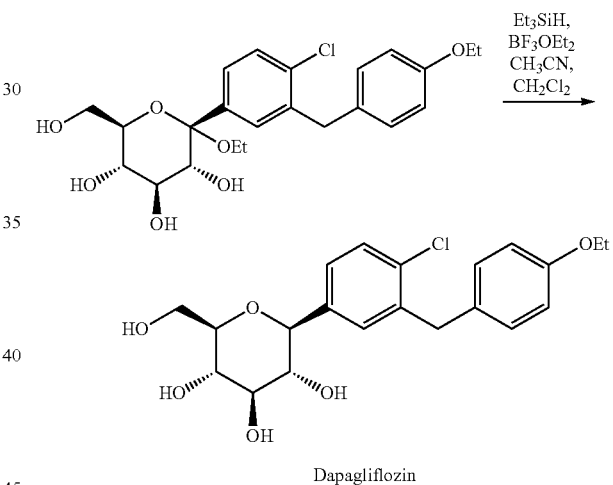

Dapagliflozin

About 8.50 g of crystal form A of (2S,3R,4S,5 S,6R)-2-(4-chloro-3-(4-ethoxybenzyl)phenyl)-2-ethoxy-6-(methylhydroxy)tetrahydro-2H-pyran-3,4,5-triol (HPLC purity: 99.45%) were weighed and added to a reactor, and then dichloromethane (60 mL) and acetonitrile (60 mL) were added. The mixture was cooled to −30° C., followed by dropwise addition of triethylsilane (12 ml) and boron trifluoride etherate (7 ml) successively. After completion of the addition, the mixture was stirred for 2 hours, and saturated aqueous solution of sodium bicarbonate was added to quench the reaction. The organic layer was separated, and the aqueous layer was extracted with ethyl acetate. The organic layers were combined, washed with saturated brine, dried over anhydrous sodium sulfate, and evaporated under reduced pressure to obtain 7.03 g of off-white solid (HPLC purity: 99.95%).

Example 7 Preparation of Dapagliflozin

About 9.0 g of (2S,3R,4S,5 S,6R)-2-(4-chloro-3-(4-ethoxybenzyl)phenyl)-2-ethoxy-6-(methylhydroxy)t etrahydro-2H-pyran-3,4,5-triol in amorphous form (HPLC purity: 90.24%) were weighed and added to a reactor, and then dichloromethane (50 mL) and acetonitrile (60 mL) were added. The mixture was cooled to −30° C., followed by dropwise addition of triethylsilane (12 ml) and boron trifluoride etherate (7 ml) successively. After completion of the addition, the mixture was stirred for 2 hours, and saturated aqueous solution of sodium bicarbonate was added to quench the reaction. The organic layer was separated, and the aqueous layer was extracted with ethyl acetate. The organic layers were combined, washed with saturated brine, dried over anhydrous sodium sulfate, evaporated under reduced pressure, and dried to obtain 6.6 g of off-white solid (HPLC purity: 99.12%).

It can be seen from Examples 6 and 7 that dapagliflozin prepared from the intermediate of the present invention can be obtained in a solid form with high purity without further acetylation purification. The reaction steps are simplified, and the yield of the product is improved.

Experimental Example 1 Stability Study

The crystal form A prepared in Example 1 was dried under vacuum at 50° C. for 3 hours, and the crystal form A was not changed.

The crystal form A prepared in Example 1 was stored at room temperature (25° C.) for 3 months, and the crystal form A was not changed.

| Test condition | Time | Crystal form | Purity |
| --- | --- | --- | --- |
| 25° C. | 0 day | Crystal form A | 99.45% |
| | 1 month | Crystal form A | 99.41% |
| | 3 months | Crystal form A | 99.43% |

Crystal form A prepared by the present invention was placed under dry conditions and room temperature for 3 months, and the crystal form was not changed, thereby improving the stability of the dapagliflozin intermediate, solving the deficiencies of the prior art, and facilitating the storage of intermediate and the improvement of product quality.

The above examples are only preferred embodiments of the present invention. It should be noted that, without departing from the technical principles of the present invention, those skilled in the art can make some improvements and modifications, which should also be considered as the protection scope of the present invention.

What is claimed is:

1. Crystal form A of a compound of formula (1),

Formula (1)

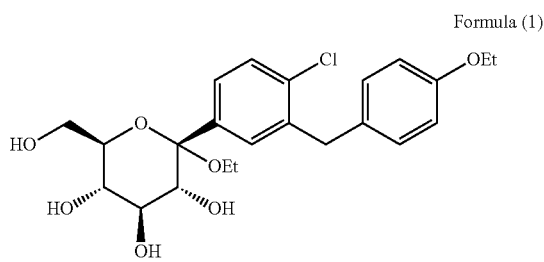 [SMILES: CCOc1ccc(Cc2cc([C@]3(OCC)O[C@H](CO)[C@@H](O)[C@H](O)[C@H]3O)ccc2Cl)cc1]

characterized by an X-ray powder diffraction spectrum comprising diffraction peaks at diffraction angles 2θ of 5.5±0.2°, 13.0±0.2°, 15.0±0.2°, 17.0±0.2°, 18.3±0.2°, 20.6±0.2°, 21.6±0.2° and 23.1±0.2°.

2. The crystal form A according to claim 1, wherein the crystal form A comprises n-propanol in an amount of about 0-15%.

3. The crystal form A according to claim 1, wherein the X-ray powder diffraction spectrum is substantially as shown in FIG. 1.

4. A method for preparing the crystal form A according to claim 1, comprising precipitating a crystal from a n-propanol solution containing 0.1 g/ml-2.0 g/ml of the compound of formula (1) at 0-30° C.

5. A method for preparing the crystal form A according to claim 1, comprising precipitating a crystal from a n-propanol solution containing 0.1 g/ml-2.0 g/ml of the compound of formula (1) at 0-30° C., and adding dropwise a $C_{5-8}$ hydrocarbon to the n-propanol solution at 0-30° C.

6. The method for preparing the crystal form A according to claim 4, wherein a concentration of the compound of formula (1) in the n-propanol solution is 0.1 g/ml-1.0 g/ml.

7. The method for preparing the crystal form A according to claim 4, wherein the method further comprises adding a seed crystal.

8. The method for preparing the crystal form A according to claim 4, wherein a crystallization temperature is 10° C.-25° C.

9. The method for preparing the crystal form A according to claim 4, wherein water is added to the n-propanol solution, and a volume of the added water is 0.05-0.5 times the mass of the compound of formula (1).

10. The method for preparing the crystal form A according to claim 5, wherein the $C_{5-8}$ hydrocarbon is selected from the group consisting of n-pentane, n-hexane, n-heptane and n-octane.

11. The method for preparing the crystal form A according to claim 5, wherein a volume of the $C_{5-8}$ hydrocarbon added is 2-40 times the mass of the compound of formula (1).

12. The crystal form A according to claim 1, wherein the X-ray powder diffraction spectrum comprises diffraction peaks at diffraction angles 2θ of 5.5±0.2°, 9.7±0.2°, 11.7±0.2°, 13.0±0.2°, 14.2±0.2°, 15.0±0.2°, 16.4±0.2°, 17.0±0.2°, 18.3±0.2°, 19.7±0.2°, 20.6±0.2°, 21.6±0.2°, 23.1±0.2°, 23.7±0.2°, 24.5±0.2°, 25.0±0.2°, 25.8±0.2°, 26.3±0.2°, 28.7±0.2°, 29.9±0.2°, 30.6±0.2°, 31.2±0.2° and 32.1±0.2°.

13. The crystal form A according to claim 2, comprising n-propanol in an amount of about 5%-7.5%.

14. The method for preparing the crystal form A according to claim 6, wherein the concentration of the compound of formula (1) in the n-propanol solution is 0.20 g/ml-0.50 g/ml.

15. The method for preparing the crystal form A according to claim 8, wherein the crystallization temperature is 20° C.-25° C.

16. The method for preparing the crystal form A according to claim 9, wherein the volume of the water added is 0.1-0.2 times the mass of the compound of formula (1).

17. The method for preparing the crystal form A according to claim 10, wherein the $C_{5-8}$ hydrocarbon is n-heptane.

18. The method for preparing the crystal form A according to claim 11, wherein the volume of the $C_{5-8}$ hydrocarbon added is 11-20 times the mass of the compound of formula (1).

* * * * *